United States Patent
Choi et al.

(10) Patent No.: US 7,110,104 B2
(45) Date of Patent: Sep. 19, 2006

(54) PANEL INSPECTION APPARATUS

(75) Inventors: Ho-seok Choi, Seoul (KR); Yong-shik Douglas Kim, Seoul (KR); Hyoung-jo Jeon, Suwon (KR); Hyeong-min Ahn, Yongin (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 10/791,798

(22) Filed: Mar. 4, 2004

(65) Prior Publication Data

US 2005/0018897 A1 Jan. 27, 2005

(30) Foreign Application Priority Data

Jul. 23, 2003 (KR) .................... 10-2003-0050449

(51) Int. Cl.
*G01N 21/88* (2006.01)
*G06K 9/00* (2006.01)

(52) U.S. Cl. .................... 356/237.1; 382/141
(58) Field of Classification Search .. 356/237.1–237.5, 356/239.1, 239.2, 121–127; 250/225, 216, 250/363.3, 336.1; 324/753, 770; 382/141, 382/154; 348/42, 47
See application file for complete search history.

(56) References Cited

U.S. PATENT DOCUMENTS

| | | | | |
|---|---|---|---|---|
| 4,629,319 A | * | 12/1986 | Clarke et al. | 356/237.2 |
| 4,870,357 A | * | 9/1989 | Young et al. | 324/770 |
| 4,894,551 A | * | 1/1990 | Kishimoto et al. | 250/559.23 |
| 4,989,981 A | * | 2/1991 | Kawamura et al. | 356/394 |
| 5,349,190 A | * | 9/1994 | Hines et al. | 250/363.05 |
| 5,638,461 A | * | 6/1997 | Fridge | 382/141 |
| 5,689,341 A | | 11/1997 | Hayashi | |
| 5,696,550 A | * | 12/1997 | Aoki et al. | 348/125 |
| 5,734,158 A | * | 3/1998 | Nagashima et al. | 250/225 |
| 5,790,247 A | * | 8/1998 | Henley et al. | 356/237.1 |
| 6,141,034 A | * | 10/2000 | McCutchen | 348/36 |
| 6,232,616 B1 | | 5/2001 | Chen et al. | |
| 6,590,643 B1 | * | 7/2003 | Kubota et al. | 356/121 |
| 6,697,514 B1 | * | 2/2004 | Kobayashi et al. | 382/141 |
| 6,782,123 B1 | * | 8/2004 | Guillon et al. | 382/154 |

FOREIGN PATENT DOCUMENTS

| | | | |
|---|---|---|---|
| FR | 2669180 A1 | * | 5/1992 |
| JP | 2003075906 A | * | 3/2003 |
| KR | 1999-17129 | | 3/1999 |
| KR | 2003-18265 | | 3/2003 |

* cited by examiner

*Primary Examiner*—Gregory J. Toatley, Jr.
*Assistant Examiner*—Sang H. Nguyen
(74) *Attorney, Agent, or Firm*—Staas & Halsey LLP (57) ABSTRACT

A panel inspection apparatus inspecting a display panel, including: a panel supporting table supporting the panel; a plurality of cameras installed being spaced from the panel supporting table and photographing the panel supported by the panel supporting table; and a rotatable camera support rotatably supporting at least one of the plurality of cameras. As a result, the number of cameras required is reduced, costing less, and easy installation.

21 Claims, 5 Drawing Sheets

PANEL INSPECTION APPARATUS

CROSS-REFERENCE TO RELATED APPLICATIONS

This application claims the benefit of Korean Patent Application No. 2003-50449, filed Jul. 23, 2003, in the Korean Intellectual Property Office, the disclosure of which is incorporated herein by reference.

BACKGROUND OF THE INVENTION

1. Field of the Invention

The present invention relates to a panel inspection apparatus, particularly, to a panel inspection apparatus having an improved support structure of a camera used to inspect a display panel.

2. Description of the Related Art

Most recent research related to display devices is focused on scaling-up the size of the screens, reducing the dimension of the screens, and reducing the weight of the screens. Various display panels, such as, an LCD (Liquid Crystal Display) and a PDP (Plasma Display Panel) have been developed as a result of such research. Accordingly, there has been a growing need for a panel inspection apparatus during the manufacturing process of the display panels.

Figure 1:
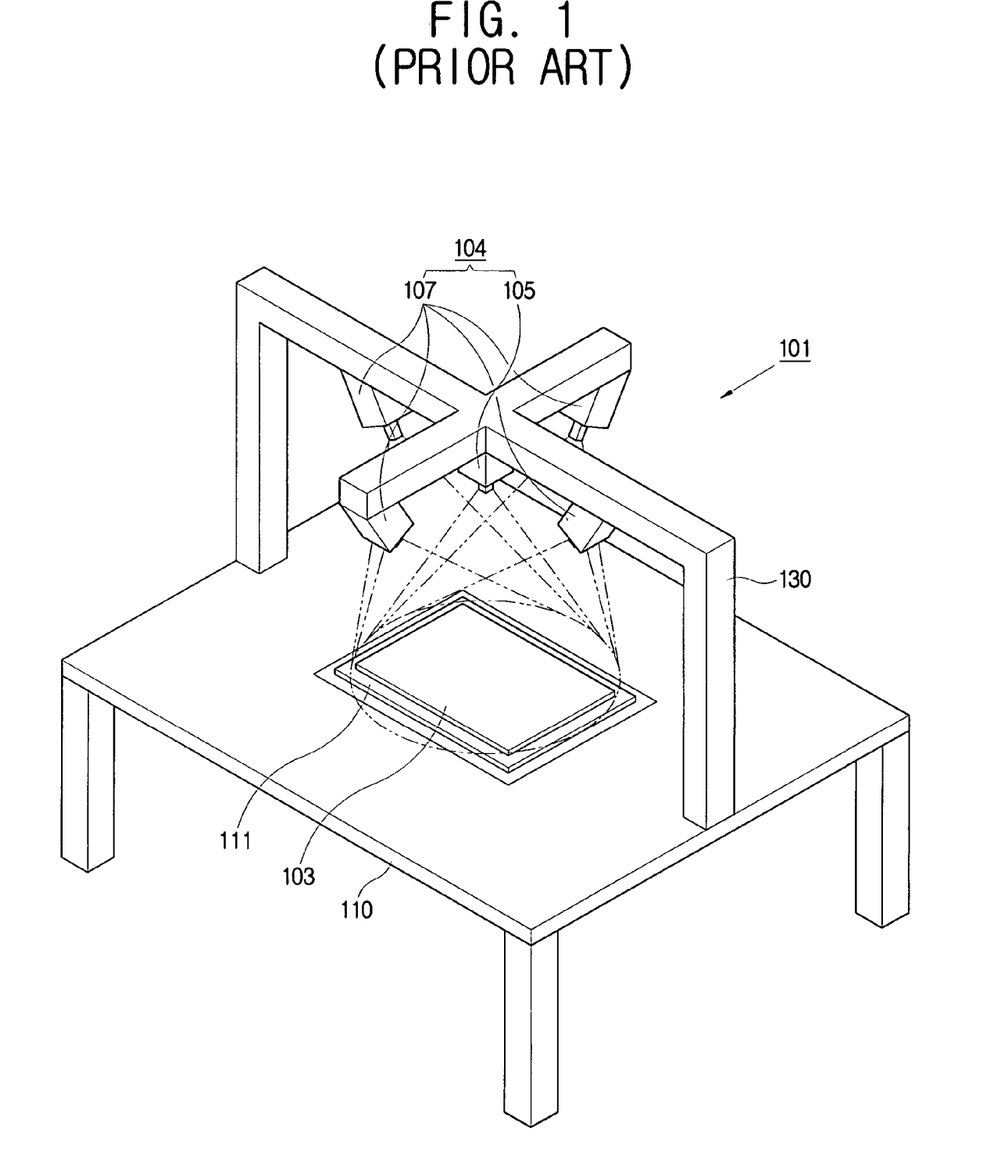
FIG. 1 is a perspective view of a conventional panel inspection apparatus.

FIG. 1 is a perspective view of a conventional panel inspection apparatus. As illustrated, a conventional panel inspection apparatus 101 comprises, a panel supporting table 110 to support a panel 103, a camera unit 104 installed above the panel supporting table 110 to photograph the panel 103 supported by the panel supporting table 110, and a camera support 130 supporting the camera unit 104.

The panel supporting table 110 is shaped like a table, and supports the panel 103 placed on a palette 111.

The camera unit 104 is installed on the camera support 130, and comprises, a first camera 105 installed to face the panel 103 perpendicular to the center of the panel 103 supported by the panel supporting table 110, and four second cameras 107 installed north, south, west, and east of the first camera 105 installed perpendicular to the center of the panel 103.

The first camera 105 installed perpendicular to the panel 103 photographs the area of the panel 103 from the direction perpendicular to the panel 103, while the four second cameras 107, installed at predetermined angles from the panel 103, photograph the panel 103 from the predetermined angles.

Accordingly, the camera unit 104 comprising the first camera 105 and the four second cameras 107 installed on the camera support 130 photograph the panel 103 supported on the panel supporting table 110 from the direction perpendicular to the panel 103 and from four different directions within the predetermined angles, respectively, to allow inspection for a defect that may occur on the panel 103, such as a fleck.

However, the conventional panel inspection apparatus is expensive because the inspection apparatus requires at least five cameras to allow inspection of the entire area of the panel 103. In addition, according to the conventional panel inspection apparatus, as the size of the panel increases, the number of cameras required to inspect the panel also increases, resulting in additional expense for installation of the additional cameras. For example, in order to inspect a 14-inch panel using the conventional panel inspection apparatus, one camera unit comprising five cameras is required, while a 21-inch panel would require at least four camera units or 20 cameras total.

SUMMARY OF THE INVENTION

Accordingly, it is an aspect of the present invention to provide a panel inspection apparatus requiring less number of cameras, thus, resulting in reduction of expenses in manufacturing the panel inspection apparatus.

The foregoing and/or other aspects of the present invention are achieved by providing a panel inspection apparatus to inspect a display panel, that comprises: a display panel supporting member to support the display panel; a plurality of cameras being spaced from the panel supporting member provided to photograph the display panel supported by the panel supporting member; and a rotatable camera support to rotatably support at least one of the plurality of cameras.

Additional aspects and advantages of the invention will be set forth in part in the description which follows and, in part, will be obvious from the description, or may be learned by practice of the invention.

According to another aspect of the invention, the plurality of cameras comprise: a first camera provided to face the display panel from a direction perpendicular to the display panel, and a second camera provided to face the display panel at an acute angle from the display panel, and being spaced from the first camera.

According to an aspect of the invention, the rotatable camera support further comprises: a driving part to rotate the second camera; a first bracket provided between the driving part and the first camera to support the first camera; and a second bracket extending from the driving part to the second camera to support the second camera.

According to yet another aspect of the invention, the second bracket supports and enables the second camera to rotate around an axis line of the first camera.

According to an aspect of the invention, the driving part comprises: a driving motor with a rotational axis line aligned to the axis line of the first camera.

According to an aspect of the invention, the second bracket is combined to the first bracket at an acute angle towards the panel supporting member.

According to an aspect of the invention, a plurality of rotatable camera supports are provided.

According to another aspect of the invention, the second camera supported by the rotatable camera support is provided so as not to interfere with the first camera supported by a nearby rotatable camera support while being rotated.

BRIEF DESCRIPTION OF THE DRAWINGS

The above and/or other aspects and advantages of the invention will become apparent, and more readily appreciated from the following description of the embodiments, taken in conjunction with the accompany drawings of which.

DETAILED DESCRIPTION OF THE PREFERRED EMBODIMENTS

Reference will now be made in detail to the embodiments of the present invention, examples of which are illustrated in the accompanying drawings, wherein like reference numerals refer to like elements throughout.

Figure 2:
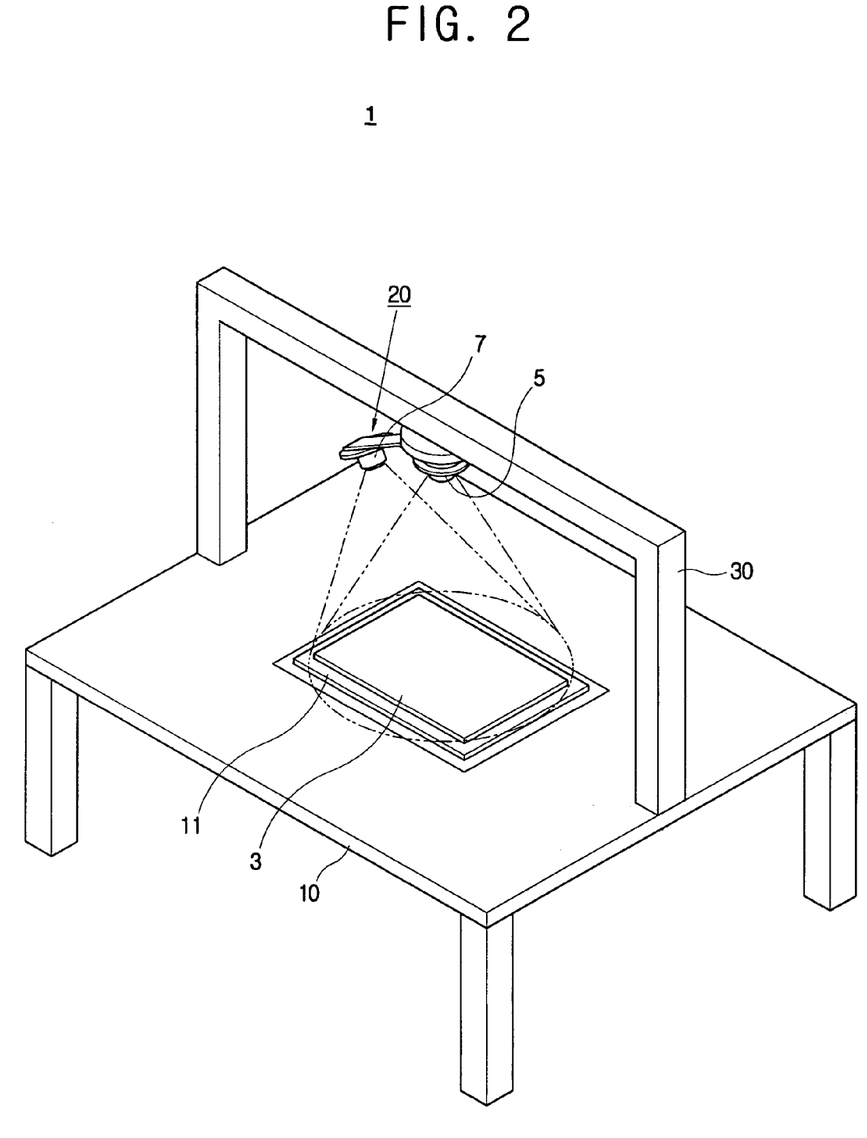
FIG. 2 is a perspective view of a panel inspection apparatus according to an aspect of the present invention.
Figure 3:
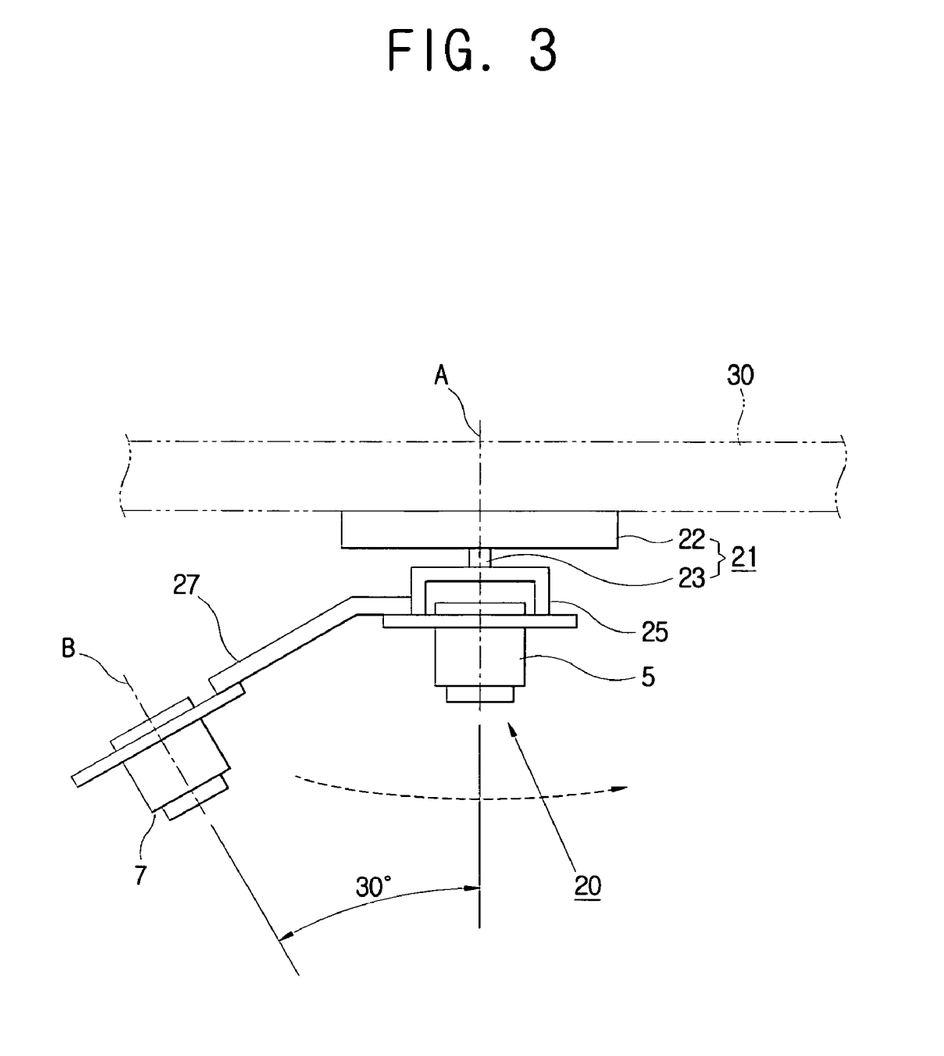
FIG. 3 is a front view of a rotatable camera support of the panel inspection apparatus.

As illustrated in FIG. 2 and FIG. 3, a panel inspection apparatus 1 according to an aspect of the present invention comprises: a panel supporting member 10 to support a display panel 3, a plurality of cameras 5 and 7 installed above the panel supporting member 10 to photograph the display panel 3 supported by the panel supporting member 10, a rotatable camera support 20 supporting the plurality of cameras 5 and 7 to rotate at least one of the plurality of cameras 5 and 7, and a camera support 30 to support the rotatable camera support 20 a distance away from the panel supporting member 10. In addition, the panel inspection apparatus 1 further comprises a monitor (not shown) with which a user can inspect the display panel 3.

Although a panel generally refers to a flat display panel, such as an LCD panel or a PDP panel, the display panel 3 described in the present invention refers to the LCD panel as an example. Herein, the size of the display panel 3 should not be larger than the camera scopes of the cameras 5 and 7.

An LCD panel installed on a display device, such as a monitor or a television, displays a picture. The LCD panel comprises a panel part including an upper glass and a lower glass, and a back light unit provided on the rear portion of the panel part to emit light towards the panel part. Liquid crystal is provided between the upper glass and the lower glass in accordance with a predetermined pattern. However, the LCD may have a fleck caused by an arranging state of the crystal liquid and infiltration of external substances, damage such as a scratch on an outer surface of the LCD, or a flaw caused by leakage of light from the back light unit to the LCD. One purpose of the panel inspection apparatus 1 according to an aspect of the present invention is to detect those defects and other similar defects.

The panel supporting member 10 is shaped like a table, and supports the display panel 3 placed on a palette 11.

The cameras 5 and 7 are installed on the rotatable camera support 20 to rotate and photograph the display panel 3 supported by the panel supporting member 10. The cameras 5 and 7 comprise, the first camera 5 installed perpendicular to the display panel 3 and facing the display panel 3, and the second camera 7 installed within a predetermined distance from the first camera 5 and facing the display panel 3 at an acute angle. Also, according to an aspect of the present invention a preferable angle between an axis of the second camera 7 and a parallel line to the display panel 3 is about 60 degrees. In other words, an angle between an axis line "B" of the second camera 7 and an axis line "A" of the first camera 5 should be about 30 degrees. However, the angle between the axis line "B" of the second camera 7 and the axis line "A" of the first camera 5 may vary based on the kind of display panel 3 or the flaw of the display panel 3 used, ranging between greater than 0 degrees and smaller than 90 degrees. Hereinbelow, the angle between the axis line "B" of the second camera 7 and the axis line "A" of the first camera 5 will be referred as a view angle. Herein, it is preferable that each photographing scope of the cameras 5 and 7 should be larger than or the same as the size of the display panel 3.

The rotatable camera support 20 installed on the camera support 30 supports the first camera 5 and the second camera 7, which are spaced by a predetermined distance from each other. Also, the rotatable camera support 20 comprises: a driving part 21 rotating the first camera 5 and the second camera 7, a first bracket 25 provided between the driving part 21 and the first camera 5 to support the first camera 5, and a second bracket 27 extending between the driving part 21 and the second camera 7 to support the second camera 7. However, according to another aspect of the invention, the first camera 5 may be combined directly to the driving part 21.

According to an aspect of the present invention, the driving part 21 is a driving motor 22 having a rotating shaft 23 to rotate the first bracket 25 and the second bracket 27.

Further, a first end of the first bracket 25 is combined to the rotating shaft 23, and a second end of the first bracket 25 is combined to a rear portion of the first camera 5 to enable the first camera 5 to rotate around the axis line "A" of the first camera 5. In addition, the axis line "A" of the first camera 5 is aligned with the rotating shaft 23 of the driving motor 22. Although the first bracket 25 is preferably screw-combined to the rotating shaft 23 and the first camera 5, it may be combined by welding, by an adhesive member or other combining elements and/or techniques.

A first end of the second bracket 27 is combined to the first bracket 25, and a second end of the second bracket 27 is combined to a rear of the second camera 7 to enable the second camera 7 to rotate around the axis line "A" of the first camera 5. Also, that the second bracket 27 and the first bracket 25 are combined within an acute angle from one another. Herein, the angle between the second bracket 27 and the first bracket 25 should be the same as the view angle, or the angle between the axis line "B" of the second camera 7 and the axis line "A" of the first camera 5. Although the second bracket 27 is preferably screw-combined to the first bracket 25 and the second camera 7, it may be combined by welding, by an adhesive member or other combining elements and/or techniques.

Hereinbelow, an operation of the panel inspection apparatus according to an aspect of the present invention will be described.

The display panel 3 accommodated in the palette 11 is placed on the panel supporting member 10. Herein, the size of the display panel 3 should be smaller than camera scope of the first camera 5 and the second camera 7. For example, the preferable size of the display panel 3 may be 14 inches. Accordingly, the driving part 21 provided on the rotatable camera support 20 rotates the first camera 5 and the second camera 7. This way, the first camera 5 photographs the display panel 3 in a direction perpendicular to the display panel 3, and the second camera 7 photographs the display panel 3 in a direction having the view angle from a perpendicular line to the display panel 3 as rotating around the axis line "A" of the first camera 5. Accordingly, the user can inspect for possible defects of the display panel 3, such as fleck caused by infiltration of external substances, the damage on the outer surface of the display panel 3, and the flaw caused by leakage of the light to the display panel 3 using a monitor (not shown).

As illustrated, the panel inspection apparatus 1 according to an aspect of the present invention has advantages, such as, reducing the number of cameras needed, reduction of cost, and easier installation compared to the conventional panel inspection apparatus by providing the rotatable camera support 20 to support and to rotate the first camera 5 and the second camera 7.

Figure 4:
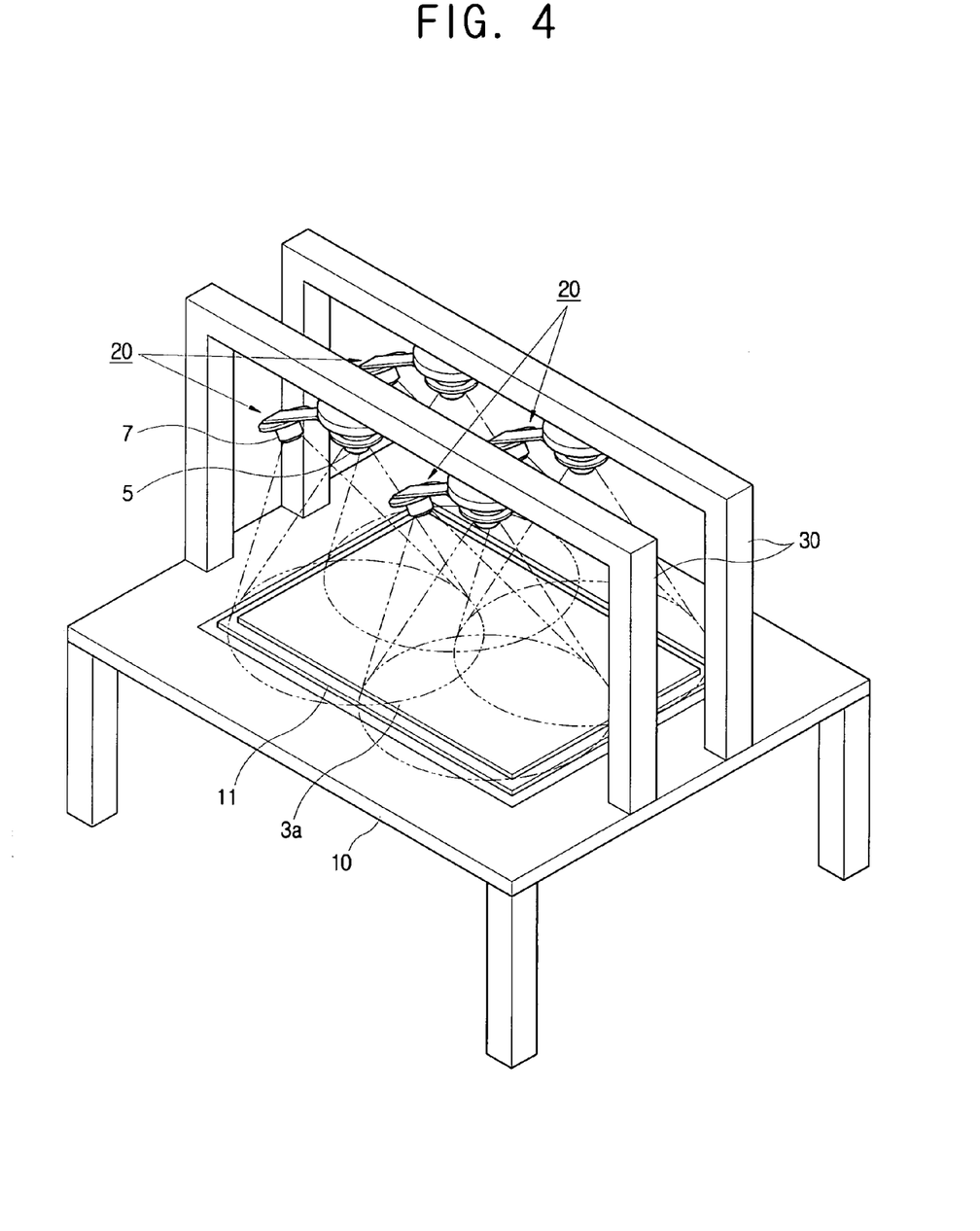
FIG. 4 is a perspective view of a panel inspection apparatus according to another aspect of the present invention.

FIG. 4 is a perspective view of a panel inspection apparatus according to another aspect of the present invention. As illustrated, a plurality of the rotatable camera supports 20 are provided to inspect a panel 3a having a larger size than the display panel 3 illustrated in FIG. 2 and FIG. 3. In order to photograph the panel 3a, a plurality of the first cameras 5, a plurality of the second cameras 7, and the plurality of the rotatable camera supports 20 are required because the photographing scopes of the first camera 5 and the second camera 7 are smaller than the size of the panel 3a.

Figure 5:
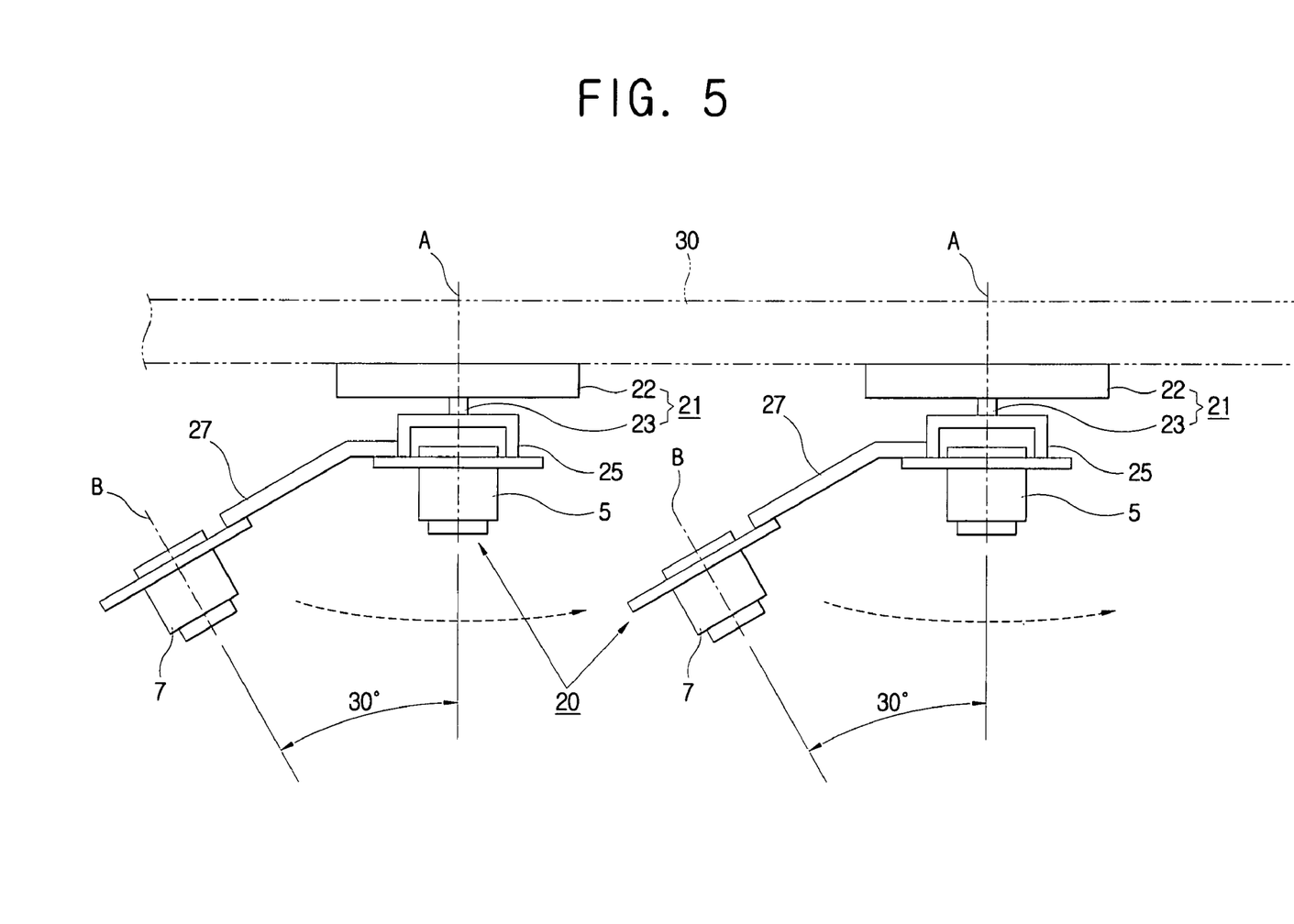
FIG. 5 is a front view of a plurality of rotatable camera supports of the panel inspection apparatus according to an aspect of the invention.

The rotatable camera support 20 supports and rotates the first camera 5 and the second camera 7. As shown in FIG. 5, the second camera 7 supported by the rotatable camera support 20 is set so as not to interfere with a second camera 7 supported by another nearby rotatable camera 20 while rotating. In other words, each second bracket 27 is combined to the respective first bracket 25 within a predetermined angle towards the panel 3a so that the second camera 7 does not collide with the second camera 7 installed on another nearby rotatable camera support 20 while rotating.

Hereinbelow, an operation of the panel inspection apparatus according to an aspect of the present invention will be described.

The panel 3a accommodated in the palette 11 is placed on the panel inspection desk 10. According to an aspect of the invention, the size of the panel 3a should be preferably larger than the camera scopes of the first camera 5 and the second camera 7. For example, the preferable size of the panel 3a may be 21 inches. The camera support 30 is provided with four rotatable camera supports 20 having eight cameras in total. The driving part 21 provided on the rotatable camera support 20 rotates the first camera 5 and the second camera 7. Accordingly, the first cameras 5 photograph the panel 3a in the direction perpendicular to the panel 3a, and the second cameras 7 photograph the panel 3a in the direction having the view angle from the perpendicular line to the panel 3a as rotating around the axis line "A" of the corresponding first cameras 5. Accordingly, the user can inspect for the defects of the panel 3a using the monitor (not shown).

As illustrated, the panel inspection apparatus according to an aspect of the present invention has advantages of reducing the number of the cameras, reducing the cost of manufacturing the panel inspection apparatus, and easier installation compared to the conventional panel inspection apparatus, by providing the plurality of the rotatable camera support 20 to support and to rotate the first cameras 5 and the second cameras 7.

In a case where a panel having a larger size than the display panel 3 needs to be inspected, as illustrated in the second aspect of the present invention, it is impossible to inspect the panel using the panel inspection apparatus with four rotatable camera supports. Accordingly, additional rotatable camera supports having a first camera 5 and a second camera 7 should be preferably added corresponding to the size of the panel. This way, the rotatable camera supports, the first camera, and the second camera can be properly added and installed according to the size of the panel.

As described, the present invention has advantages of reducing the number of cameras, reducing cost, and easy installation.

Although a few embodiments of the present invention have been shown and described, it will be appreciated by those skilled in the art that changes may be made in these embodiments without departing from the principles and spirit of the invention, the scope of which is defined in the appended claims and their equivalents.

What is claimed is:

1. A panel inspection apparatus to inspect a display panel, comprising:
   a panel supporting member to support the display panel;
   a plurality of cameras, being spaced from the panel supporting member, provided to photograph the panel supported by the panel supporting member; and
   a rotatable camera support to rotatably support at least one of the plurality of cameras for circumferential rotation, with respect to at least another one of the plurality of cameras, during an inspection of the display panel.

2. The panel inspection apparatus according to claim 1, wherein the plurality of cameras further comprise:
   a first camera provided to face the display panel from a direction perpendicular to the panel; and
   a second camera provided to face the display panel at an acute angle to the display panel, and being spaced from the first camera.

3. The panel inspection apparatus according to claim 2, further comprising:
   at least one additional rotatable camera support.

4. The panel inspection apparatus according to claim 3, wherein the second camera supported by the rotatable camera support is provided so as not to interfere with the first camera supported by an adjacent one of the rotatable camera supports while being rotated.

5. A panel inspection apparatus to inspect a display panel, comprising:
   a panel supporting member to support the display panel;
   a plurality of cameras, being spaced from the panel supporting member, provided to photograph the panel supported by the panel supporting member; and
   a rotatable camera support to rotatably support at least one of the plurality of cameras in circumferential direction with respect to at least another one of the plurality of cameras,
   wherein the plurality of cameras further comprise:
   a first camera provided to face the display panel from a direction perpendicular to the panel; and
   a second camera provided to face the display panel at an acute angle to the display panel, and being spaced from the first camera, and
   wherein the rotatable camera support further comprises:
   a driving part to rotate the second camera;
   a first bracket provided between the driving part and the first camera to support the first camera; and
   a second bracket extending from the driving part to the second camera to support the second camera.

6. The panel inspection apparatus according to claim 5, wherein the second bracket supports and enables the second camera to rotate around an axis line of the first camera.

7. The panel inspection apparatus according to claim 6, wherein the driving part further comprises:
   a driving motor with a rotational axis line aligned to the axis line of the first camera.

8. The panel inspection apparatus according to claim 6, wherein the second bracket is combined to the first bracket at an acute angle towards the panel supporting member.

9. The panel inspection apparatus according to claim 5, wherein the driving part rotates both the first camera and the second camera.

10. A panel inspection apparatus of a display panel, comprising:

a panel supporting member to support the display panel;
a plurality of cameras installed above the display panel;
a rotatable camera support to rotatably support at least one of the plurality of cameras for circumferential rotation, with respect to at least another one of the plurality of cameras, during an inspection of the display panel; and
a camera support member to support the rotatable camera support above the panel supporting member.

11. The panel inspection apparatus according to claim 10, wherein the camera support member supports the rotatable camera support a predetermined distance away from the panel supporting member.

12. The panel inspection apparatus according to claim 10, wherein the size of the display panel is not larger than the camera scope of each of the plurality of cameras.

13. The panel inspection apparatus according to claim 10, wherein the panel supporting member is shaped like a table.

14. The panel inspection apparatus according to claim 10, wherein the plurality of cameras further comprise:
a first camera provided to face the display panel from a direction perpendicular to the display; and
a second camera provided facing the display panel at an acute angle from the camera support and an axis line of the first camera.

15. The panel inspection apparatus according to claim 14, wherein the first camera is installed within a predetermined distance of the second camera.

16. The panel inspection apparatus according to claim 14, wherein an axis line of the second camera and the axis line of the first camera are separated by 30 degrees.

17. The panel inspection apparatus according to claim 14, further comprising:
a driving part to rotate the first camera and second camera.

18. A panel inspection apparatus of a display panel, comprising:
a panel supporting member to support the display panel;
a plurality of cameras installed above the display panel;
a rotatable camera support to rotatably support at least one of the plurality of cameras in circumferential direction with respect to at least another one of the plurality of cameras;
a camera support member to support the rotatable camera support above the panel supporting member,
wherein the plurality of cameras further comprise a first camera provided to face the display panel from a direction perpendicular to the display and a second camera provided facing the display panel at an acute angle from the camera support and an axis line of the first camera, and;
a driving part to rotate the first camera and second camera;
a first bracket provided between the driving part and the first camera to support the first camera; and
a second bracket extending from the driving part to the second camera to support the second camera.

19. A panel inspection apparatus to inspect a display panel, comprising:
a panel inspection desk provided to support the display panel;
a plurality of first cameras;
a plurality of second cameras;
a plurality of rotatable camera supports provided to rotatably support and rotate the at least one of the plurality of first cameras in circumferential direction with respect to at least another one of the plurality of first cameras and at least one of the plurality of second cameras in circumferential direction with respect to at least another one of the plurality of second cameras; and
a camera support member to support the plurality of rotatable cameras.

20. The panel inspection apparatus according to claim 19, wherein the at least one of the plurality of first cameras has an optical axis concurrent with an axis of rotation of the rotatable camera support.

21. The panel inspection apparatus according to claim 19, wherein
the at least one of the plurality of second cameras rotates around the at least one of the plurality of first cameras, and
the at least one of the plurality of second cameras has an optical axis at an acute angle relative to that of the at least one of the plurality of first camera.

* * * * *

UNITED STATES PATENT AND TRADEMARK OFFICE
CERTIFICATE OF CORRECTION

| | | |
|---|---|---|
| PATENT NO. | : 7,110,104 B2 | Page 1 of 1 |
| APPLICATION NO. | : 10/791798 | |
| DATED | : September 19, 2006 | |
| INVENTOR(S) | : Ho-Seok Choi et al. | |

It is certified that error appears in the above-identified patent and that said Letters Patent is hereby corrected as shown below:

Column 6, Line 46, after "and" insert --,--.

Signed and Sealed this

Thirteenth Day of February, 2007

JON W. DUDAS
*Director of the United States Patent and Trademark Office*